US006524608B2

(12) United States Patent
Ottoboni et al.

(10) Patent No.: US 6,524,608 B2
(45) Date of Patent: Feb. 25, 2003

(54) INTRAVESICAL DRUG DELIVERY SYSTEM

(75) Inventors: Thomas B. Ottoboni, Belmont, CA (US); Ronald K. Yamamoto, San Francisco, CA (US); Stanley R. Conston, San Carlos, CA (US)

(73) Assignee: Point Biomedical Corporation, San Carlos, CA (US)

( * ) Notice: Subject to any disclaimer, the term of this patent is extended or adjusted under 35 U.S.C. 154(b) by 0 days.

(21) Appl. No.: 09/819,117

(22) Filed: Mar. 27, 2001

(65) Prior Publication Data

US 2001/0019719 A1 Sep. 6, 2001

Related U.S. Application Data

(60) Division of application No. 09/525,609, filed on Mar. 14, 2000, now Pat. No. 6,207,180, which is a division of application No. 09/054,154, filed on Apr. 2, 1998, now Pat. No. 6,039,967, which is a continuation-in-part of application No. 08/833,247, filed on Apr. 3, 1997, now abandoned.

(51) Int. Cl.[7] .............................. A61F 2/02; A61F 6/06; A61K 47/30

(52) U.S. Cl. ...................... 424/426; 424/430; 514/772.3

(58) Field of Search ................................. 424/426, 430; 514/772.3

(56) References Cited

U.S. PATENT DOCUMENTS

| | | |
|---|---|---|
| 5,021,241 A | 6/1991 | Yamahira et al. |
| 5,326,761 A | 7/1994 | Rozier |

FOREIGN PATENT DOCUMENTS

| | | |
|---|---|---|
| EP | 0 437 368 A1 | 7/1991 |
| JP | 51-140582 | 12/1976 |
| WO | WO 917745 | 11/1991 |

OTHER PUBLICATIONS

Ekstrom et al., "Intravesical Instillation of Drugs in Patients with Detrusor Hyperactivity," Depts. Of Urology and Clinical Pharmacology, University Hospital, Lund, Sweden, 1992, pp. 11–67.

Massad et al., "The Pharmacokinetics of Intervesical and Oral Oxybutynin Chloride," *J. Urol.*, 1992, 148:595–597.

Okado et al., "Study of Intervesical Stick (Part 1): Method of Preparation and Dissolution Test for Active Component," *Yakugaku Zasshi*, 1985, 105(10):1001–1003.

Okado et al., "Study of Intervesical Stick (Part 1): Development of Intervesical Stick, and Manufacture of Instillator," Nichihitsunyokaishi, 1985, 76(2):197–203.

PCT Search Report, PCT/US98/06445, mailed Jul. 17, 1998.

*Primary Examiner*—Carlos Azpuru
(74) *Attorney, Agent, or Firm*—Fish & Richardson P.C.

(57) ABSTRACT

Bioerodible, sustained release preparations are provided for placement into the bladder through the urethra which provided sustained release of drugs. Configurations are provided which are insertable through a catheter, such as a coiled filament, patch or a flowable gel. The device is bioeroded during or after the sustained release of the drug such that there is no blockage of the urinary tract while the device is in place within the bladder.

40 Claims, 5 Drawing Sheets

11 10 12

INTRAVESICAL DRUG DELIVERY SYSTEM

This is a divisional if U.S. patent application Ser. No. 09/525,609, filed Mar. 14, 2000, issued as U.S. Pat. No. 6,207,180 on Mar. 27, 2001; which is a divisional of U.S. patent application Ser. No. 09/054,154, filed Apr. 2, 1998, issued as U.S. Pat. No. 6,039,967 on Mar. 21, 2000; which is a continuation-in-part of U.S. patent application Ser. No. 08/833,247, filed Apr. 3, 1997, now abandoned which is incorporated by reference in its entirety.

BACKGROUND OF THE INVENTION

The invention is directed to a system for the controlled and sustained delivery of therapeutic agents to the human bladder.

There are numerous conditions of the bladder or urinary tract, such as cancer, inflammation, infection or incontinence, that may be treated by pharmaceutically active compounds. Many of these compounds are presently orally administered, however, that is a disadvantage in that systemic delivery is used to treat a condition or disease that is possibly more effectively treated by local applications. Also, many of the drugs used for the treatment of urge incontinence are anti-cholinergics with potent adverse side effects. An intravesical administration would accomplish a high concentration of the drug locally in the bladder wall or urine without producing a high serum concentration.

The following are some typical or currently used intravesical treatments of the bladder. For the treatment of bladder cancer, the drug doxorubicin is instilled directly into the bladder. A mycobacterium, Bacillus Calmette-Guerin, is also administered intravesically for treatment of carcinoma located in the bladder. For interstitial cystitis, DMSO is instilled intravesically to provide symptomatic relief. For incontinence, the anticholinergic drug oxybutynin chloride has been reported to have been used.

In these cases of intravesical delivery, the drug is simply instilled by solution into the bladder. A disadvantage with this approach is that for chronic conditions such as incontinence, the patient must be repeatedly catheterized, thus requiring frequent attention by trained medical staff. Also, the potential for infection is increased by repeated catheterization into the bladder, which can be as often as several times per day.

Okado et al., Yakugaku Zasshi, 105(10), 1001–1003 (1985); Nichihitsunyokaishi, 76(2), 197–203 (1985); tested an intravesical stick made of beeswax and surfactants, incorporating the drug bleomycin. However, it was observed that elution of the drug from the stick was rather rapid, about 1 to 3 days, and particles of the stick remain in the bladder, which could lead to blockage of the urinary tract or to the formation of kernels for bladder stones.

Accordingly, it would be desirable to provide a sustained or controlled delivery device that is capable of delivery of the drug for an extended period of time, preferably one week or longer, with the device biodegrading or bioeroding over time to clear the bladder.

SUMMARY OF THE INVENTION

The invention provides a bioerodible, sustained-release preparation for placement into the bladder through the urethra. The preparation may have a specific gravity less than or equal to that of the specific gravity range of human urine. The preparation comprises a pharmaceutically active ingredient and at least one bioerodible, pharmaceutically acceptable carrier, which is capable of sustaining delivery of the active ingredient within the bladder and is bioerodible and excretable without blockage of the urinary tract.

DESCRIPTION OF THE PREFERRED EMBODIMENTS

Figure 1:
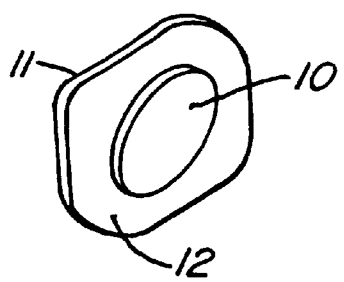
FIG. 1 shows a preferred device according to the invention comprising a reservoir with a backing material.

A bioerodible carrier according to the present invention means a carrier which is readily dissolved, eroded, or is subject to degradation in the bladder. In one embodiment, the carrier material according to the present invention does not substantially decompose, disperse, disintegrate or dissolve in the bladder until most of the drug has been released.

In another embodiment, portions of the device will decompose, disperse, disintegrate or dissolve in a controlled manner so as to provide a controlled release of the drug contained in the decomposing portions.

Many carrier materials which are suitable for these embodiments are natural products, such as keratin, salol, triglycerides, fatty acids, lipids, latexes, as well as derivatives of natural products such as modified collagens, modified gelatins, regenerated proteins, celluloses, cellulose derivatives, salts of cellulose derivatives, alkaline or alkaline earth salts of cellulose acetate phthalate, ammonium salts of hydroxypropyl methyl cellulose phthalate, polysaccharides, synthetic polymers, such as, polyglycolic acid and derivatives of polyethylene glycol, polycaprolactone, polylactic acid, and copolymers thereof; materials such as starch, fatty alcohols, alginate polymers, albumin, calcium caseinate, calcium polypectate or gellan gum.

The carrier for the active ingredient may made by any number of methods known in the art for forming materials which contain medicaments. For example, a filament can be made with a centrifugal extrusion device or by coextrusion. The filament texture is preferably a porous, open cell foam. Filaments may also be made by interfacial polymerization processes, known in the art, for example, for the manufacture of nylon. The filament may be formed into random or regular coils, hoops, spheres, and the like.

Production by extrusion also enables the changing of the amount of the drug contained in the filament along the length of the filament, thereby allowing control of the dosage delivered in the bladder. Extrusion also enables the containment of the drug in one portion of the filament and the use of one or more additional drugs or an alternate formulation of the same drug, in other portions of the filament for the same purpose. The filament may contain two or more incompatible drugs in spatially distinct portions of the filament. The drugs may also be encapsulated in the carrier.

As discussed above, the time release of the drug may be controlled by diffusion from the carrier and/or erosion of the carrier, which simultaneously releases the drug. The bioerosion mechanism may be controlled by serially degrading segments of a filament. This may be accomplished, for example, by providing an outer layer of slowly bioerodible material with a core of rapidly bioerodible material containing the drug. Thus the exposed ends of the core will preferentially bioerode. At various points along the filament, weakened portions may be provided by which an outer layer may be detached once the core has been bioeroded, thereby causing the filament to be eroded in segments starting from the exposed ends.

In the case of carriers in the shape of sheets or spheres, the carrier materials may be formed in the desired shape or formed into sheets and cut into the appropriate form.

The carrier material will be typically one of two types. One type bioerodes rather uniformly over time, so that the bioerosion of the carrier is also the primary mechanism for releasing the drug into the bladder. The second type is a material which essentially remains intact during a substantial portion of the release period of the drug. The mechanism of release of the drug is by diffusion or other mechanism which does not require the carrier to be concurrently bioeroded. However, in such cases, shortly after the drug has been depleted from the carrier, erosion should proceed in order to avoid the necessity of removing the device from the bladder.

In either of these mechanisms of drug release, the sustained delivery of the drug into the bladder will be for an extended period, longer than about three days and referably, at least about one week. For incontinence, cancer, or other chronic conditions, it is preferred that the drug be delivered over a period up to about one month. The carrier materials, containing or impregnated with the drug, may have a specific gravity less than or equal to that of urine, which is normally about 1.005 gm/ml to 1.033 gm/ml at 25° C. This allows the device to be neutrally buoyant or float in the urine of the bladder to minimize the occurrence of blockage of the urethra.

A preferred embodiment of the delivery system is a flowable gel or set-in-place system that can be introduced into the bladder via a cannula. By set-in-place, it is meant that the gel sets when introduced into the bladder. In this system the drug is dispersed or placed in a carrier (microsphere, liposome, emulsion, etc.) which in turn is dispersed in a gel-forming system, such as gellan gum, a polysaccharide derived fermentation of *Pseudomonas elodea*, available as Gelrite® from Kelco. Solutions of this material gel when contacted with an ionic environment, which, in this case, is the urine in the bladder. The preferred gel is an ionic gel-in-place type, such as gellan gum. In this case, the retention mechanism is the buoyancy of the device, so its specific gravity must be less than or equal to that of human urine. The ionic strength of the urine causes, for example, a solution of gellan gum to gel. Since oils have a density less than 1 gm/ml, a lipid emulsion component of the gel has a density less than 1.0 gm/ml. Thus, the combination of the gel, having a density approximately equal to the surrounding medium, and a lipid, having a density less than 1.0 gm/ml, affords a device with a net density less than the surrounding medium. The gellan gum will slowly solubilize into the urine and be excreted, as will the lipid droplets.

The gelling system will preferably contain, in addition to the phase changing component (gellan, gum, alginate, CMC, polyacrylic acid, carboxymethyl chitosan, and the like), a rheology modifier. This modifier will be a water-soluble high molecular weight polymer such as polyethylene oxide, PVP, dextran, dextrose, PEO/PVP copolymers, hyaluronic acid, hydroxyethyl cellulose, polyacrylamide, PVA, chitosan, gelatin or other high molecular weight water-soluble polymers. The molecular weight of the rheology modifier is preferably in the range of about $10^5$–$10^7$ daltons.

When using a lipid carrier or release rate modifier, described below, the drug formulation is typically introduced into the lipid phase by mixing a salt form of the drug in water in the oil phase and increasing the pH. Deprotonation of the drug causes selective partition into the lipid phase, then the remainder of the components (the gelling component) are added.

Alternatively, an un-ionized form of the drug is dissolved in the lipid phase, the release modifier is added, then the mixture is emulsified. The remaining components are then added.

The second preferred embodiment of a delivery system is a device physically capable of being retained in the bladder without blocking the urinary tract. These devices are retained in the bladder by their shape such as a filament. These systems must be formed from a bioerodible polymer that will reliably release drug over the predefined period of time and completely erode during that period. It is not necessary that this type of device have a density less, than human urine.

In one modified embodiment of a delivery system, at least one surface of the device may be coated with a mucoadhesive in order that the device adhere to the wall of the bladder. Mucoadhesive coated microspheres are preferred. Such mucoadhesives may be selected from a number of known synthetic, naturally-occurring or modified naturally-occurring substances which exhibit of tackiness. The adhesive must be biocompatible, that is, nontoxic and/or inert, within the bladder. The adhesive will also be compatible with the material forming the carrier, as well as the drug. Substances appropriate for use as mucoadhesives include, but are not limited to, carboxymethyl and hydroxypropyl methyl cellulose, and other cellulose derivatives; tragacanth, caraya, locust bean and other synthetic and naturally gums such as algin, chitosan, starches, pectins, and naturally-occurring resins, polyvinyl pyrrolidone, polyvinyl alcohol, and polyacrylic acid.

Specific preferred embodiments will now be discussed in connection with the figures, but it is not intended that the devices be limited by the accompanying figures.

Referring to FIG. 1, there is shown a device consisting of a drug reservoir 10 having a backing 12 bearing a mucoadhesive 11 on the back surface.

Figure 2:
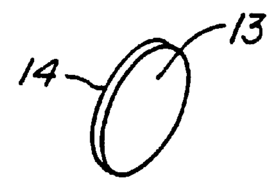
FIG. 2 shows a preferred device according to the invention comprising a reservoir with an adhesive coating.

FIG. 2 shows a device according to the invention comprising a reservoir 13 to which is directly applied the mucoadhesive coating 14 so that the device may be attached to the wall of the bladder.

Figure 3:
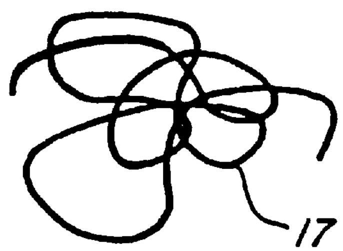
FIG. 3 shows an embodiment or device of the invention comprising a randomly oriented filament network.

FIG. 3 shows a randomly oriented filament network 17 containing the drug. This filament may be saturated with the drug, and may have a coating to control diffusion rate. The filament may also be segmented.

Figure 4:
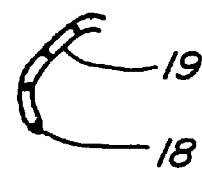
FIG. 4 shows an expanded view of one end of a filament, showing a segmented structure.

In FIG. 4, a view of an end of a segmented filament is shown. The drug is shown to be contained within an axial drug reservoir 18 in the filament. The network comprises segments 19 with erodible linking sections between the segments which allow the segments to detach as the drug reservoir is depleted within that segment.

Figure 5:
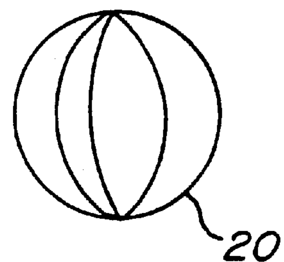
FIG. 5 shows a preferred device according to the invention comprising a filament network having multiple segments which form a spherical cage.

FIG. 5 shows another network of filaments forming a spherical cage 20.

It is a feature of the present invention that the devices containing the drug are insertable into the bladder through the urethra by a catheter. Thus, the devices are preferably made of flexible or gel-like material so that they may be coiled or compressed to fit through a catheter of sufficient size. Upon being released from the catheter, the devices will have a sufficient shape memory to uncoil or expand into the shapes shown, for example, in the accompanying figures. By retaining such shapes, the devices per se will not be drawn into the urethra to cause blockage, but will be retained within the bladder for an extended period of time. For devices having a mucoadhesive coating, by virtue of the random motion within the bladder, the mucoadhesive surface will eventually contact the bladder wall, thus achieving the desired implantation.

The drugs which may be utilized include, but are not limited to the following. Drugs for urge incontinence include dicyclomine, desmopressin, oxybutynin, estrogen, terodiline, propantheline, doxepin, imipramine and flavoxate. Other drugs include phenylpropanolamine, terazosin, praxosin, pseudoephedrine and bethanechol. Oxybutynin and impranine are the two most widely used for urge incontinence and are preferred. For treatment of bladder cancer, doxorubicin is preferred. In addition, Bacillus Calmette-Guerin, a mycobacterium, may be utilized for treatment of carcinoma in situ of the bladder. For treatment of interstitial cystitis, DMSO or an anesthetic agent may be utilized. Thus, it is contemplated that any drug may be utilized for the treatment of any condition related to the bladder or urethral tract, including urge incontinence, cancer, infections, inflammation, and the like.

The dosages utilized will depend upon the protocol required for the treatment of the particular condition and the patient. Particularly by use of filaments, variation in dosages is readily available since it is merely a case of using a longer or shorter length.

In a preferred embodiment, the drug will be combined with a carrier and, optionally, a release modifier which alters the release of the drug into bladder. Typical carriers include corn oil, soybean oil, canola oil, safflower oil, polypropylene glycol and other natural oils. Typical release rate modifiers include oleic, stearic, palmitic and other saturated or unsaturated fatty acids; cholic acid, diacylphosphoric acid and other hydrophobic anionic compounds; phospholipids, diesters of citric acid, benzoic acid, substituted benzoic acids, substituted phenols, ion exchange polymers, Eudragit™, methacrylate-methacrylic acid copolymers, Tweens™, Spans™, lecithin, alkyl nitrates, ethyl or methyl cellulose.

Therefore, preferably a gel-in-place drug delivery system will include two components: the gelling components containing the phase change material and, optionally, a rheology modifier; and the drug release component containing the drug, carrier and, optionally, a release rate modifier.

The drug release rate may also be regulated by the carrier per se when there is a chemical affinity of the drug to the carrier. Alternatively, a release rate modifier may be incorporated into the carrier, forming complexes or conjugates of carrier and modifier, and the like.

The drug release component may also comprise a drug unmodified by release modifiers. Such a component, for example, may comprise the drug dispersed in a solid lipophilic system such as anionic wax, self-emulsifying wax, cholesterol, fatty acid esters, beeswax or tallow.

A reservoir device, such as that shown in FIG. 1 or 2 may be utilized where the reservoir can contain a much larger dose of drug compared to, for example, the filament configuration. If a gel is used to provide sustained delivery of the drug it can be readily sterilized during preparation, then aseptically loaded into a sterile delivery device. Gels may be formulated as low viscosity dispersions with the drug or drug carrier which, when in contact with urine in the bladder, then gel or precipitate to form a solid filament or mass, thereby forming a delivery vehicle which can be retained in the bladder.

The device must have a configuration, not limited to those disclosed, such that it does not block the flow of urine from the bladder or cause excessive mechanical irritation to the bladder wall.

By way of illustration, the following examples are given for the preparation of devices according to the present invention. However, these are for purposes of illustration and are not intended in any way to limit the scope of the invention.

EXAMPLE 1

A solution of oxybutynin chloride (titer: 50 mg/ml) (1 ml) and 2% collagen (50 grams) is homogeneously mixed with stirring while preventing occurrence of foam. The mixture is lyophilized and pulverized at a low temperature using liquid nitrogen. The pulverized product is formed under compression to give a needle-shaped preparation.

EXAMPLE 2

Materials of Example 1 are prepared with the addition of glycerol in order to impart flexibility to the device. The mixture is extruded into a filament and then dried. The filament may be randomly wound and inserted through a catheter for insertion into the bladder.

EXAMPLE 3

(1) Preparation of an Ionic Gel-in-Place Polymer Solution

In a 100 ml beaker, 49.5 ml of deionized water is heated to 70° C. Then 0.5 grams of purified gellan gum (Gelrite™, Kelco Inc.) is added while agitating the water with an overhead mixer and a propeller style mixing blade. After mixing for 10 minutes, the solution is filtered through a cellulose filter to remove any undissolved gellan gum.

(2) Preparation of a Mucoadhesive Gel-in-Place Polymer Solution

In a 100 ml beaker, 49.5 ml of deionized water is heated to 70° C. Then 0.5 grams of purified gellan gum (Gelrite™, Kelco Inc.) is added while agitating the water with an overhead mixer and a propeller style mixing blade. After mixing for an additional 10 minutes to the stirred solution slowly is added 1.25 grams of polyacrylic acid (Carbopol 934P) and mixing is continued for an additional 10 minutes. The solution is filtered through a cellulose filter to remove any undissolved gellan gum.

EXAMPLE 4

Preparation of Drug Containing Emulsion

In a 100 ml plastic beaker, 1.25 grams of oleic acid is combined with 3.75 grams of purified corn oil. To the oil mixture, 0.25 grams of Tween 80 is added and mixed well. While mixing with a rotor stator type high shear mixer (Virtis, Cyclone), 42.25 ml of water is slowly added to the blend. The mixing is continued throughout the addition process and for an additional minute once the addition of the water is complete. The resulting emulsion is mixed with a magnetic stir bar. Then 2.5 grams of oxybutynin chloride is added to the emulsion and mixed thoroughly. The pH of the emulsion is adjusted to 6.5 with 1 N sodium hydroxide.

EXAMPLE 5

Preparation of Hollow Drug Loaded Particles

DL-polylactic acid (5 grams) is dissolved in dichloromethane (95 grams) with gentle mixing. Oxybutynin chloride (2.5 grams) is then added to the polymer solution and dissolved. The drug/polymer solution is spray-dried in a spray drier (Yamato) to yield hollow drug loaded polylactic acid microspheres.

EXAMPLE 6

(1) Preparation of a Mucoadhesive, Ionic Gel-in-Place Delivery System

The filtered solution of gellan gum/polyacrylic acid solution (example 3) is added into a 200 ml beaker. The solution is warmed to approximately 40° C. The mixing head of the overhead mixer is placed into the beaker to begin agitation. The drug containing emulsion (example 4) is slowly added to the gum solution. Mixing is continued for an additional 3 minutes after addition is complete. The solution is cooled to room temperature. When gelled, this composition will have a net density less than that of human urine.

(2) Preparation of Gel-in-Place Delivery System

The filtered solution of 1% gellan gum solution (example 3) is placed into a 200 ml beaker and warmed to approximately 40° C. The mixing head of the overhead mixer is placed into the beaker to begin agitation. The drug containing emulsion (example 4) is slowly added to the gum solution. Mixing is continued for an additional 3 minutes after addition is complete. The solution is cooled to room temperature.

(3) Preparation of Gel-in-Place Delivery System

The microspheres (5 grams from example 5) are dispersed into 50 ml deionized water containing 0.25% Pluronic™ F-127. The filtered solution of 1% gellan gum solution (example 1) is placed into a 200 ml beaker and warmed to approximately 40° C. The mixing head of the overhead mixer is placed into the beaker to begin agitation. The drug containing microsphere solution is slowly added to the gum solution. Mixing is continued for an additional 3 minutes after addition is complete. The solution is cooled to room temperature. Aliquots of 1 ml of the microsphere/gum dispersion are placed into 5 ml lyophilization vials, lyophilized and stored under vacuum.

EXAMPLE 7

Preparation of Filament Delivery System

Poly(d,l-lactic acid-co-glycolic acid) copolymer is blended with oxybutynin chloride in a 1:3 ratio. The polymer/drug blend is extruded into a 0.5 millimeter diameter filament using a microextruder. The filaments are cut into 10 cm lengths and wound into a tight bundle. The resulting bundle is placed into the tip of a catheter. The loaded catheter is sterilized by γ-irradiation with a 2.5 Mrad dose.

EXAMPLE 8

Preparation of a 3% Oxybutynin Delivery System (A)

(a) Preparation of Gel-in-Place Polymer Solution

In a 150 ml beaker, 49 ml of deionized water is heated to 95° C., and 1 gram of purified gellan gum (Gelrite™, Kelco Inc.) is slowly added while agitating the water with an overhead mixer and a propeller style mixing blade. After mixing for 10 minutes, the solution is filtered through a cellulose filter to remove any undissolved gellan gum. The gum solution is autoclaved at 121° C. for 20 minutes. The solution is allowed to cool and 0.1 grams of disodium EDTA and 0.1 grams of sodium polyphosphate are added to the gel solution.

(b) Preparation of Drug Containing Emulsion

In a 100 ml beaker, 3 grams oxybutynin chloride and 20 ml of deionized water are combined. Then 18.75 grams of soybean oil are added to the oxybutynin solution and mixed. The pH of the mixture is adjusted to 7.5. The mixture is centrifuged and the oil phase is separated. The water layer is discarded. Separately 1 gram of Pluronic F68 is dissolved in 20 grams of water. To this is added 6.25 grams oleic acid and the mixture is homogenized. The oleic acid emulsion and the soybean oil mixture prepared above are combined and homogenized with a high shear mixer. The pH of the resulting emulsion is adjusted to 6.5 with 1 gram of 1N NaOH.

(c) Preparation of Gel-in-Place Delivery System

The solution of gellan gum solution (a) is added into a 200 ml beaker. The solution is warmed to approximately 40° C. The mixing head of the overhead mixer is placed into the beaker to begin agitation. The drug containing emulsion (b) is added slowly to the gum solution. Mixing is continued for an additional 3 minutes after addition is complete. The solution is cooled to room temperature. The pH is adjusted to 6.5 with 1N HCl or NaOH as necessary.

(d) Preparation of Viscosity Modified Gel-in-Place Polymer Solution

In a 150 ml beaker, 48.5 ml of deionized water was heated to 95° C. To this was slowly added 1 gram of purified gellan gum (Gelrite™, Kelco Inc.) and 0.5 grams of polyethylene oxide (MW=$7\times10^6$) while agitating the water with an overhead mixer and a propeller style mixing blade. After mixing for 10 minutes, the solution was filtered through a cellulose filter to remove any undissolved gellan gum. The gum solution was autoclaved at 121° C. for 20 minutes. The solution was allowed to cool and 0.1 grams of disodium EDTA and 0.1 grams of sodium polyphosphate were added.

EXAMPLE 9

Preparation of a 1% Oxybutynin Delivery System (B)

A 1% oxybutynin delivery system was prepared in the manner described in Example 8 except that the amount of oxybutynin chloride used was 1 gram and that 1 gram of Pluronic F68 was dissolved into 22 grams of water.

EXAMPLE 10

Release Studies

General Method

A sample of 0.25 grams of the desired delivery system (a 3% oxybutynin system is used unless otherwise indicated) is introduced into 250 mL of an artificial urine (composed of 500 mM solution of sodium chloride containing 50 mM phosphate buffer) via an 18 gage cannula. The pH of the elution buffer is 6.2 unless otherwise listed. Aliquots of the elution buffer are collected at the indicated times during a 24 hour period and analyzed by high performance liquid chromatography.

Release Study 1: Effect of Buffer pH

Figure 6:
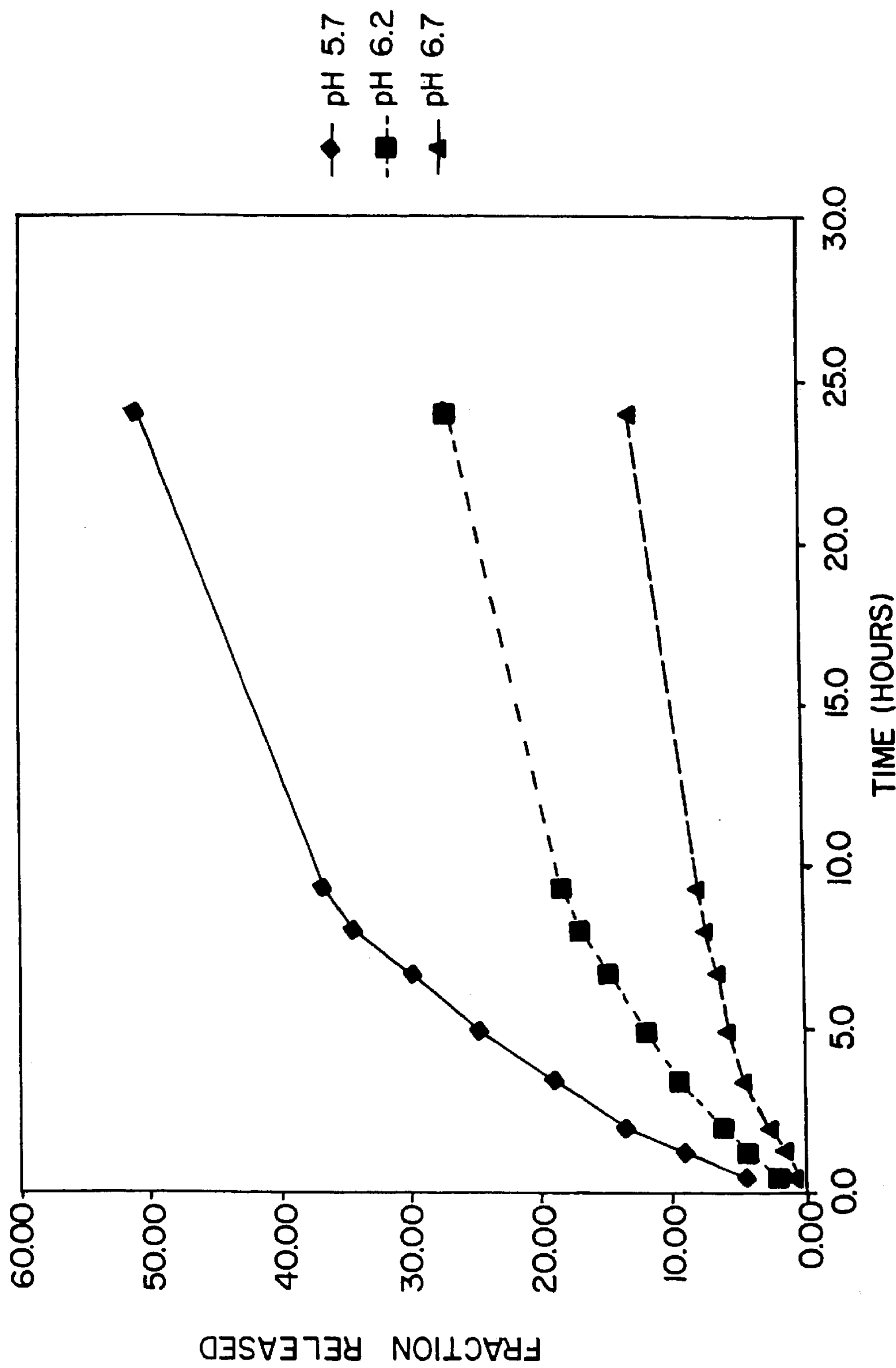
FIG. 6 shows the rate of release of oxybutynin from a gel-in-place system in simulated urine solutions at pH 5.7, 6.2 and 6.7.

The system was introduced into a solution of the standard buffer, a buffer where the pH was adjusted to 5.7 and in a third buffer system where the pH was adjusted to 6.7. Amount of drug release from each was determined and plotted in FIG. 6 as a fraction of the total drug introduced into the buffer. The release rate of drug from the system was observed to increase with decreasing pH of the elusion buffer.

Release Study 2: Effect of Cannula Size

Figure 7:
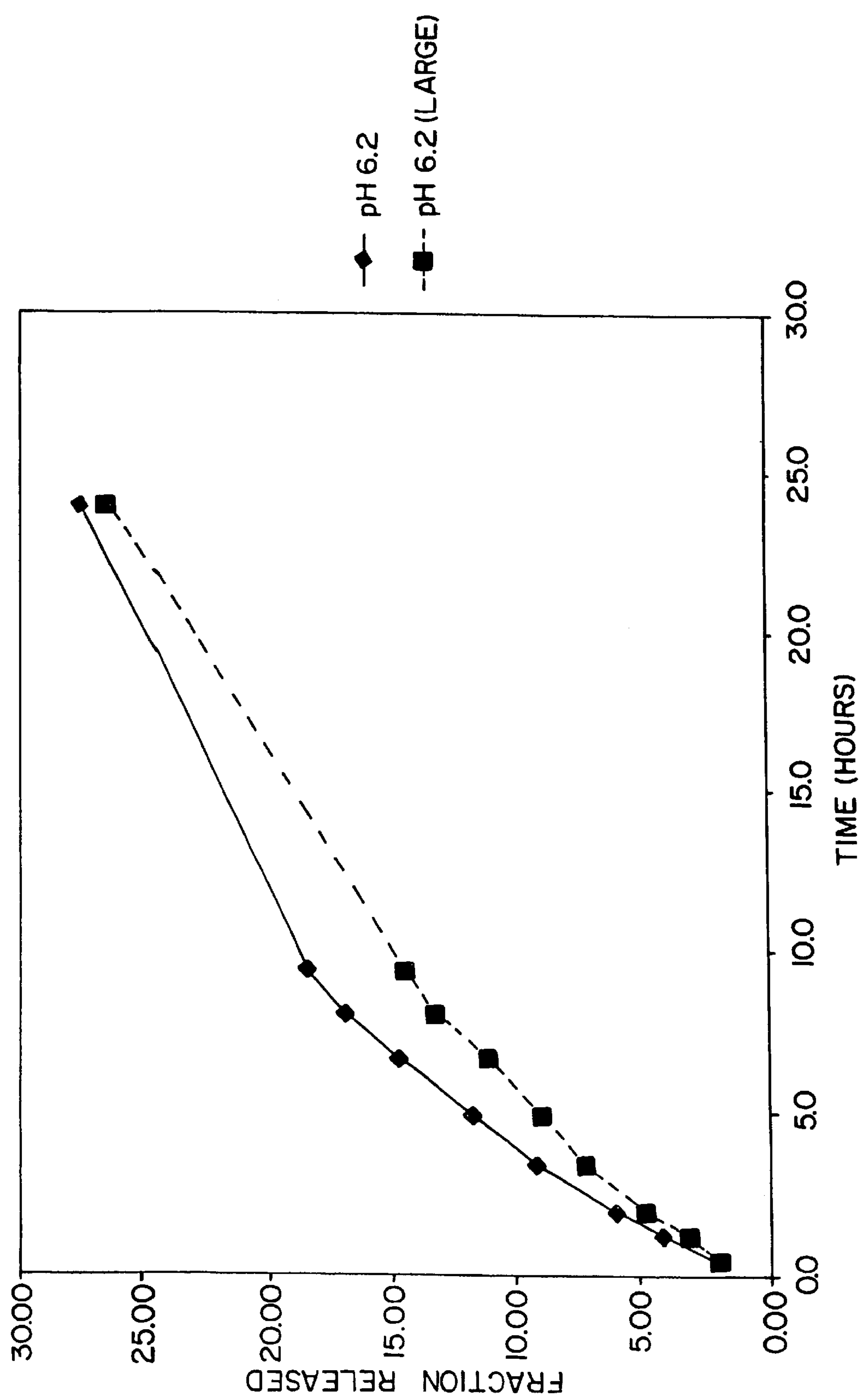
FIG. 7 shows the rate of release of oxybutynin from two gels of different surface areas.

The system was introduced into the buffer using a 18 gage cannula (0.8 mm diameter) as described above and into a second buffer system using a 3 mm diameter cannula. Drug release from each system was determined and plotted as a fraction of the total drug introduced into the system. The drug release was observed to be slower from the system delivered from the 3 mm cannula. See FIG. 7.

Release study 3: Effect of Varying Drug Content

Figure 8:
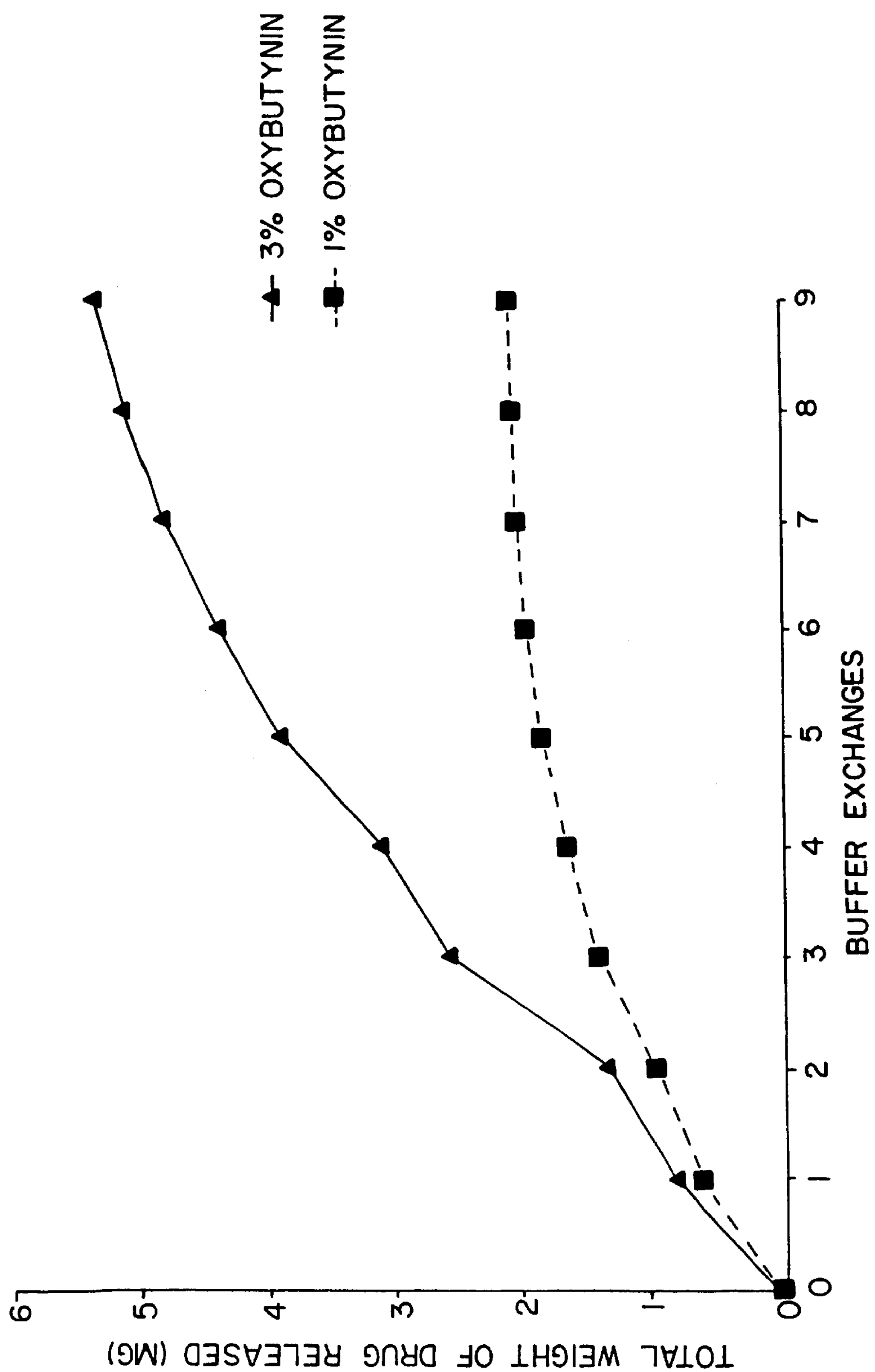
FIG. 8 shows the rate of release of oxybutynin from two gels having concentration of 3% and 1% oxybutynin.

Release studies were conducted on the two systems described above (A and B). In this case, rather than sampling the buffer over a 24 hour period, the buffer was sampled every 24 hours and immediately was exchanged with fresh buffer to model the release over several days. A greater amount of drug was released from the 3% oxybutynin system than was released from the 1% oxybutynin system. The amount released from the 3% system was observed to be more consistent over the nine buffer exchanges than the amount released from the 1% system which released fractionally more drug early in the study. See FIG. 8.

Release Study 4: Effect of Modifier Concentration

Figure 9:
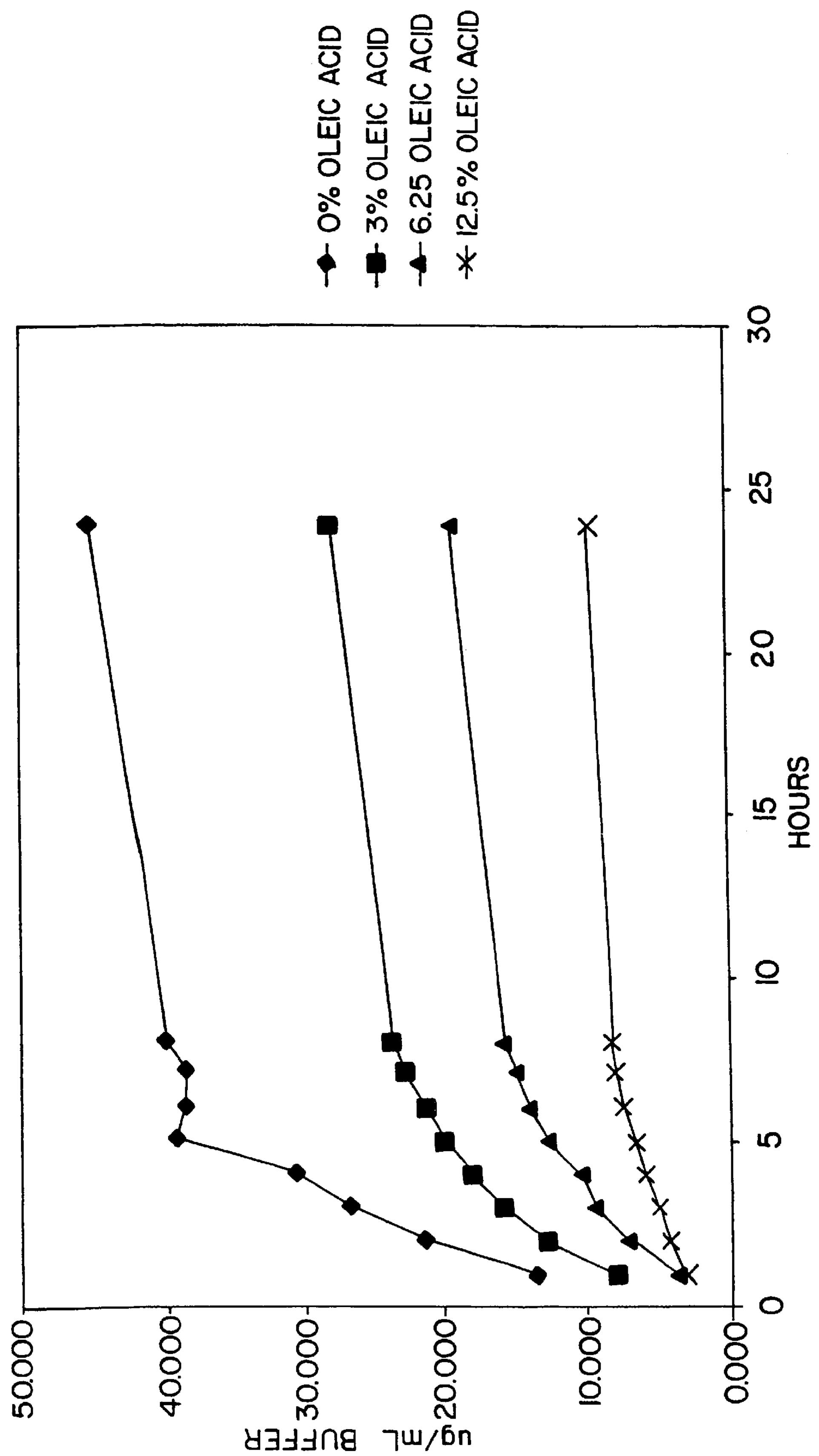
FIG. 9 shows the rate of release of oxybutynin from gels having 3%, 6.25%, 12.5% and no oleic acid as a release rate modifier.

Formulations containing 0, 3, 6.25 and 12.5% wt/wt oleic acid were prepared as described above, except that the appropriate amount of oleic acid was used. Release studies were conducted on each formulation and the amount of drug release was determined and plotted in FIG. 9 as the concentration in the buffer versus time. It was observed that less drug is released from the system as the modifier concentration is increased.

What is claimed is:

1. A method of treatment of incontinence comprising the step of placing in the bladder of a patient by catheterization of the urethra a bioerodible, sustained-release preparation comprising a pharmaceutically active ingredient and a bioerodible pharmaceutically acceptable carrier capable of sustained delivery within the bladder of said active ingredient and excretable through the urinary tract after bioerosion.

2. A method according to claim 1 wherein said preparation has a specific gravity less than about 1.005 at 25° C.

3. A method according to claim 1 wherein said active ingredient is selected from the group consisting of oxybutynin, imipramnine, dicyclomine, desmopressin, estrogen, terodiline, propantheline, doxepin, and flavoxate.

4. A method according to claim 3 wherein said active ingredient comprises oxybutynin.

5. A method according to claim 1 wherein said preparation further comprises a mucoadhesive surface adherable to the endothelium of the bladder.

6. A method according to claim 5 wherein said preparation comprises a patch.

7. A method according to claim 5 wherein said preparation comprises a tablet.

8. A method according to claim 1 wherein said preparation comprises an expandable filament which in unexpanded form is passable through the urethra for insertion and in expanded form is retained within the bladder.

9. A method according to claim 8 wherein said filament comprises a coil.

10. A method according to claim 8 wherein said filament comprises a hoop.

11. A method according to claim 9 wherein said filament comprises a random coil.

12. A method according to claim 8 wherein said filament comprises a spherical cage wherein the filaments meet at poles of the sphere.

13. A method according to claim 8 wherein said filament is progressively degradable from it ends.

14. A method according to claim 8 wherein said filament is progressively degradable in discrete segments.

15. A method according to claim 8 wherein said filament forms a porous open cell foam.

16. A method according to claim 1 wherein said preparation further comprises a reservoir from which said active ingredient is controllably released.

17. A method according to claim 1 wherein said preparation comprises a gel.

18. A method according to claim 17 wherein said gel is formed upon contact with urine in said bladder.

19. A method according to claim 17 wherein said gel is mucoadhesive.

20. A method according to claim 18 wherein said gel has a density less than urine.

21. A method according to claim 17 wherein said active ingredient is in a carrier dispersed in said gel.

22. A method according to claim 21 wherein said carrier comprises microsphers, liposomes or an emulsion.

23. A method according to claim 1 wherein said active ingredient is released from said carrier before said carrier is completely bioeroded.

24. A method according to claim 1 wherein said active ingredient is controllably released as said carrier is bioeroded.

25. A method according to claim 1 wherein said preparation further comprises a rate release modifier to alter the release rate of said active ingredient.

26. A method according to claim 25 wherein the release rate of said sustained delivery is regulated by a chemical affinity of said active ingredient to said carrier.

27. A method according to claim 25 wherein said rate release modifier is incorporated into said carrier.

28. A method according to claim 25 wherein said modifier is selected from the group consisting of saturated fatty acids, unsaturated fatty acids, cholic acid, diacyl phosphoric acid, phospholipids, esters and citric acid, benzoic acid, substitutd benzoic acids, substituted phenols, ion exchange polymers, methacrylate-methacrylic acid copolymers, lecithin, alkyl nitrates and alkyl cellulose.

29. A method according to claim 28 wherein said modifier comprises an unsaturated fatty acid.

30. A method according to claim 29 wherein said fatty acid comprises oleic acid.

31. A method according to claim 17 wherein said gel comprises a phase-changing component and a rheology-modifying component.

32. A method according to claim 31 wherein said phase changing component is selected from the group consisting of gellan gum, alginate, carboxymethyl cellulose, polyacrylic acid and carboxymethyl chitosan.

33. A method according to claim 32 wherein said phase changing component comprises gellan gum.

34. A method according to claim 31 wherein said rheology-modifying component is selected from the group consisting of polyethylene oxide, polyvinylpolypropylene, dextran, dextrose, polyethylene oxide/polyvinyl polypropylene copolymers, hyaluronic acid, hydroxyethyl cellulose, polyacrylamide, polyvinyl alcohol, chitosan and gelatin.

35. A method according to claim 34 wherein said rheology modifying component comprises polyethylene oxide.

36. A method according to claim 18 wherein said active ingredient comprises oxybutynin and said carrier comprises gellan gum.

37. A method according to claim 36 wherein said preparation further comprises oleic acid.

38. A method according to claim 36 wherein said preparation further comprises soybean oil.

39. A method according to claim 37 wherein said preparation further comprises polyethylene oxide.

40. A method according to claim 39 wherein said polyethylene oxide has a molecular weight of about $7\times10^6$ daltons.

* * * * *